United States Patent [19]

Sullivan et al.

[11] Patent Number: 5,388,580
[45] Date of Patent: Feb. 14, 1995

[54] HEAD HOLDER FOR MAGNETIC RESONANCE IMAGING/SPECTROSCOPY SYSTEM

[75] Inventors: James V. Sullivan, Bowie; Joseph A. Frank, Potomac; Roland W. Seldon, Rockville, all of Md.

[73] Assignee: The United States of America as represented by the Department of Health and Human Services, Washington, D.C.

[21] Appl. No.: 932,842

[22] Filed: Aug. 19, 1992

[51] Int. Cl.⁶ .............................................. A61B 5/055
[52] U.S. Cl. ............................... 128/653.1; 128/653.5; 128/845; 128/869; 5/622; 378/20; 378/68; 378/208
[58] Field of Search ............... 128/653.5, 653.2, 653.1, 128/845, 857, 869; 324/318, 309; 378/20, 68, 208, 209; 2/417, 418, 419, 421; D29/12, 15, 16; 5/600, 621, 622; 607/109

[56] References Cited

U.S. PATENT DOCUMENTS

| | | | |
|---|---|---|---|
| 2,964,753 | 12/1960 | Austin | 2/417 |
| 3,851,644 | 12/1974 | Slagle | 128/134 |
| 3,866,244 | 2/1975 | Ruck | 2/419 |
| 4,064,401 | 12/1977 | Marden | 378/208 |
| 4,071,231 | 1/1978 | Kok | 269/325 |
| 4,182,322 | 1/1980 | Miller | 128/133 |
| 4,256,112 | 3/1981 | Kopf et al. | 606/130 |
| 4,341,220 | 7/1982 | Perry | 128/630 |
| 4,400,820 | 8/1983 | O'Dell et al. | 128/845 |
| 4,454,870 | 6/1984 | Schwentker | 128/869 |
| 4,463,758 | 8/1984 | Patil et al. | 128/303 |
| 4,616,814 | 10/1986 | Harwood-Nash et al. | 378/208 |
| 4,850,003 | 7/1989 | Huebeck et al. | 378/179 |
| 4,928,711 | 5/1990 | Williams | 128/869 |
| 4,979,519 | 12/1990 | Chavarria et al. | 128/857 |
| 4,986,282 | 1/1991 | Stackhouse et al. | 128/857 |
| 5,005,578 | 4/1991 | Greer et al. | 128/653.2 |
| 5,010,898 | 4/1991 | de Kanawati et al. | 128/845 |
| 5,081,665 | 1/1992 | Kostich | 378/208 |
| 5,085,219 | 2/1992 | Ortendahl et al. | 128/653.5 |
| 5,199,940 | 4/1993 | Morris et al. | 128/845 |
| 5,233,713 | 8/1993 | Murphy et al. | 5/622 |

FOREIGN PATENT DOCUMENTS 2213066  8/1989  United Kingdom ................ 606/130

*Primary Examiner*—Krista M. Pfaffle
*Attorney, Agent, or Firm*—Townsend and Townsend Khourie and Crew

[57] ABSTRACT

A head holder with the following characteristics: it is compatible with MR (no metallic parts); it is adjustable for use with adults and children; it does not produce any degradation of imaging or spectroscopy raw data; it does not induce claustrophobia; it can be used as a fixation device for cervical spine MR examinations; and it can operate with any MR unit. A strap is placed around the head of the patient at the forehead, is tightened, and then the head with band attached is positioned for optimal comfort and examining advantage. Lock screws are then tightened, holding the head comfortably in three-dimensional space. Only a single band is placed over the forehead of the person and the rest of the fixation is provided by adjusting and locking screws located in the base and along the sides of the holder. This prevents the patient from being able to rotate his or her head from side to side or up and down. The holder is designed to fit into the MR table. This is a major improvement over existing devices in that it provides for patient comfort while providing adequate head support and fixation.

17 Claims, 2 Drawing Sheets

HEAD HOLDER FOR MAGNETIC RESONANCE IMAGING/SPECTROSCOPY SYSTEM

This invention relates to improvements in the placement of a patient in a correct position in a magnetic resonance imaging/spectroscopy apparatus and, more particularly, to an improved holder for the head of a patient in such an apparatus.

BACKGROUND OF THE INVENTION

One of the major problems confronting clinicians and scientists in the field of magnetic resonance imaging (MRI) and magnetic resonance spectroscopy (MRS) is movements of the patient during the operation of such a system. Movements artifacts lead to degradation of image quality, making it often impossible for a radiologist interpreting the images to render a correct diagnosis. Movement artifacts seem to occur in patients undergoing MR scans of the brain in which the individual cannot hold still during the operation of the imaging or spectroscopy apparatus due to clinical condition of the patient or due to the fact that the patient is a child who may not be able to follow commands to hold his or her head still during operation of the apparatus. MR spectroscopy of the brain is also sensitive to head movement, making the information obtained in examination lasting up to 1.5 hours impossible to interpret.

Almost all MR units come with a head holder in which the patient places his or her head while undergoing an MR examination. Conventional head holders usually only provide basic support of the patient's head, still allowing head movements within the head coil. Another type of head fixation device commonly used for MR activities is a face mask which is made of pliable plastic and which is molded to conform to the face and then threaded or attached to a holder forming a part of the MR unit.

The difficulty with this type of device is that in placing a mask over the patient's face, there is increased incidence of patient non-compliance due to feelings of claustrophobia. This device is also difficult to use with children.

Other types of devices usually do not provide head fixation in three planes. Stereotaxic head holders require screws to be placed in the patient's skull and are usually used only pre-operatively prior to neurosurgical procedures.

Because of the foregoing drawbacks, a need exists for improvements in head holders for MRI or MRS apparatus. The present invention satisfies this need.

SUMMARY OF THE INVENTION

The present invention is directed to a head holder with the following characteristics: it is compatible with MR (no metallic parts); it is adjustable for use with examinations of the heads of adults and children; it does not produce any degradation of imaging or spectroscopy raw data; it does not induce or aggravate any symptoms of claustrophobia; it can be used as a fixation device for cervical spine MR examinations; and it can be adapted to fit and operate with any MR unit.

In the construction of the device or holder, the present invention is simple in construction and it is lightweight, easily and quickly fitted onto an individual's head by technologists, and is comfortable to wear while still providing the necessary head and spine support needed for motion sensitive MR exams. The basic idea behind the head unit or holder is that it is made to fit into the head coil of an MR unit and that a multi-adjustable strap is placed around the head of the patient at the forehead, is tightened, and then the head with band attached is positioned for optimal comfort and examining advantage. Lock screws are then tightened, holding the head comfortably in three-dimensional space. The design of this holder prevents the head from moving in three degrees of freedom.

The major improvement of the present invention over the prior art holder as described above is that only a single band is placed over the forehead of the person and the rest of the fixation is provided by adjusting and locking screws located in the base and along the sides of the holder. This prevents the patient from being able to rotate his or her head from side to side or up and down (chin to chest). In addition, the holder is specifically designed to fit into the MR table. This is a major improvement over existing devices in that it provides for patient comfort while providing adequate head support, alignment, and fixation. In an experimental usage of the device, in which over one hundred normal volunteers and patients participated, a number of individuals have been able to fall asleep during an MR exam. This is indicative of the degree of head comfort and support provided by the present invention.

The primary object of the present invention is to provide an improved head holder for an MR imaging or spectroscopy apparatus wherein the holder is compatible with the MR apparatus, is adjustable for use with the head of adults and children, and does not produce any degradation of imaging and spectroscopic raw data.

Another object of the present invention is to provide a holder of the type described wherein the holder does not induce or aggravate any symptoms of claustrophobia, it can be used as a fixation device for cervical spine MR examination and can be adapted to fit any commercially available MR unit.

Still a further object of the present invention is to provide a holder for an MR apparatus of the type described wherein the holder is of lightweight construction, can be easily and quickly fitted onto the patient's head and is comfortable to wear while still providing the necessary head and spine support needed for motion sensitive MR exams.

A further object of the present invention is to provide a head holder of the aforesaid character wherein the holder is made to fit onto the head coil of an MR unit with an adjustable strap placed around the head of a patient and tightened for optimal comfort and examining advantage.

Other objects of the present invention will become apparent as the following specification progresses, reference being had to the accompanying drawings for an illustration of the invention.

DETAILED DESCRIPTION OF THE DRAWINGS

Figure 1:
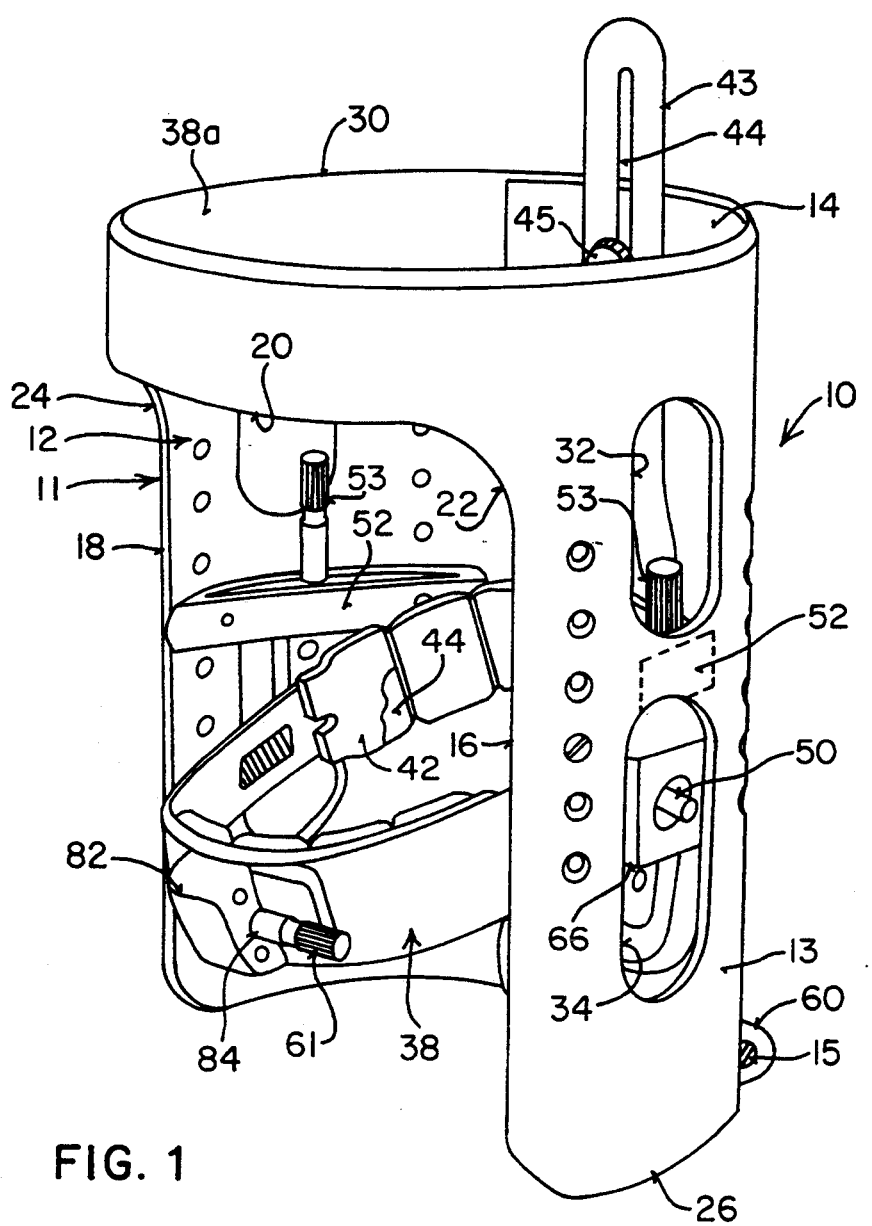
FIG. 1 is a perspective view of the head holder of the present invention.

The head holder of the present invention is broadly denoted by the numeral 10 and is partially cylindrical in shape. The holder is rigid and typically is comprised of a body made from a non-metallic material. The body has an opening 12 (FIG. 1) for the face of the wearer. A cylindrical back part 14 extends from a vertical edge 16 around the back of the body 11 to a vertical edge 18 on the opposite side of the body. Vertical edges 16 and 18 are edges which merge smoothly with a top, horizontal edge 20 by virtue of a pair of curved edge segments 22 and 24. The lower ends of edges 16 and 18 merge smoothly with a bottom, semi-circular edge 26 as shown in FIG. 1.

The top of body 11 is open and is defined by an upper circular edge 30. Each side of body 11 has a pair of elongated access openings 32 and 34, the openings 32 being substantially horizontally aligned with each other. The top annular member of body 11 provides rigidity for body 11. Body 11 essentially defines a helmet attachable to an MR system.

A padded, adjustable head band 38 is provided generally within body 11. The head band is formed from a flexible, yieldable material, such as a suitable plastic, such as nylon. A number of yieldable, flexible pads 42 are secured in any suitable manner, such as by adhesive 44 to the inner peripheral surface 46 of the head band. The padded sections 42 are of any suitable construction, such as fabric material filled with stuffing material, such as cotton or the like to make the attachment of the head band to the head of the wearer a comfortable fit.

The head band member 38 is secured at three locations to body 11. Firstly, a stabilizing bar 43 is rigidly secured in any suitable manner to body 11 near the rear end thereof. Stabilizer bar 43 has a vertical slot 44 for receiving a fastener 45 for adjustably positioning the rear part of band 40 at a predetermined height which is comfortable to the wearer of the body.

Figure 2:
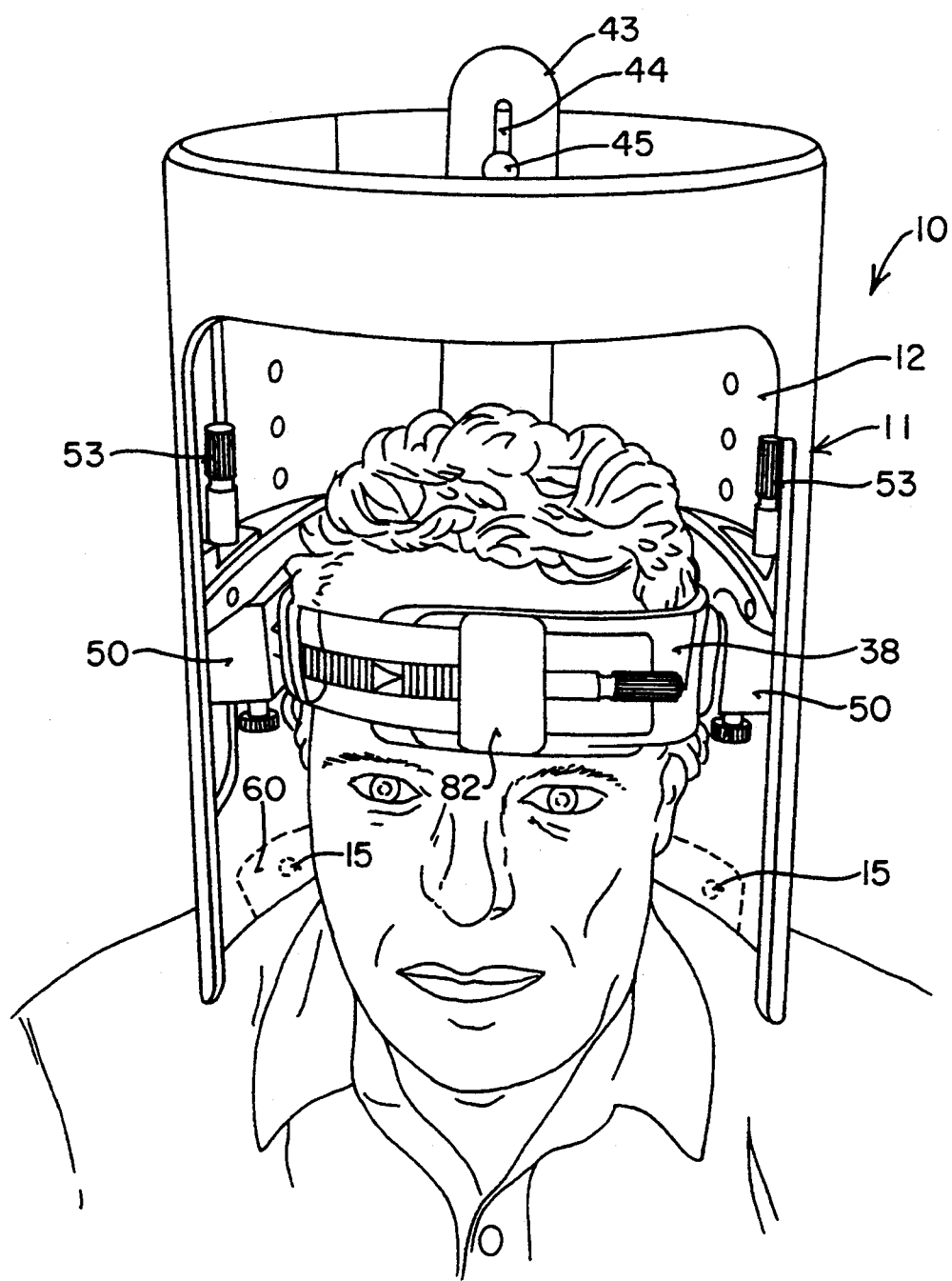
FIG. 2 is a perspective view of the holder on the head of a patient to hold the head of the patient against movement during an MR exam.

Stabilizer bar 43 extends upwardly from edge 30 of body 11 so that the height of the rear portion of the head band 38 can be varied as much as possible. Thus, each of the opposed sides of band 38 is provided with a head band ball and joint assembly 50. Assembly 50 is carried by a side support 52 on each side, respectively, of the central axis of member 38. Each side support 52 is secured by a clamp screw 53 which also serves to center the head band 38 with reference to the facial opening 12 (FIG. 1). Screw holes 55 in the sides of body 11 receive fasteners which are coupled to side supports 52 for gross positioning of the head band 38. Ball joint assemblies 50 are accessible through slots 34 which shiftably mount the sides of head band 38 on respective side supports 52. A worm assembly 82 shiftably interconnects the ends of the band 38 to tighten the band on the forehead as shown in FIG. 2. Screw 61 adjusts worm assembly 82.

Figures 3, 4:
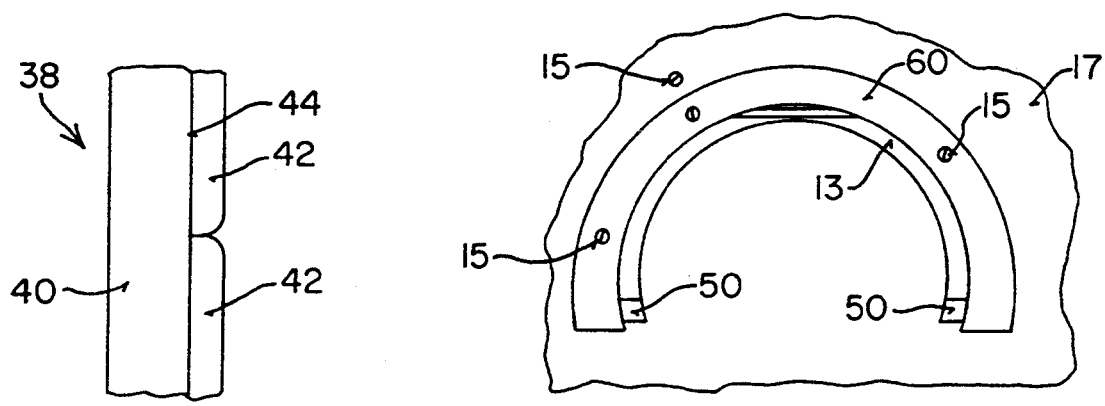
FIG. 3 is a cross-sectional view taken along line 3—3 of FIG. 1.
FIG. 4 is a schematic top plan view of the band for wrapping around the forehead of the patient.

Body 11 has an outer flange 60 as shown in FIG. 4. Flange 60 is integral with wall 13 and the flange is secured by fasteners 15 to the flat upper surface 17 of support or table 19 which is to be used during the operation of an MR machine.

The sides of body 11 have a pair of side grooves 66 by means of which the height of the side portion of the head band 38 can be adjusted with respect to a given reference such as a top edge 20 of body 11 (FIG. 1). All adjustments can be made while a patient is removed from the device and is in a sitting position. The device is removed from the machine for this purpose and then reattached, such as reattaching the patient to the table with the MR cradle and bracket allowing for very fine head band tightness and/or adjustment. The ability to move the head band in any direction within the rigid frame provides for the differences or irregularities in patient anatomy and can enhance the study through precise head movements or positions. No other device on the present market is currently available which affords the universal, comfortable, yet rigid non-claustrophobic head fixation capabilities of this head assembly.

In use, an approximate fit of the holder to the patient's head may be made while the patient is in a sitting position. Then the holder is removed from the head and attached to the MR machine table. The patient is placed in the holder for additional adjustments. All adjustments can also be made with the patient in a reclining position. The head band 38 is flexible yet rigid when secured to the MR table, allowing firm yet comfortable fit of all head sizes. The head band worm assembly 82 and adjustment screw 84 allows fine head band tightness adjustment. The patient, if able, can make this adjustment to his or her comfort level. The ability to move the head band in any direction within the rigid holder housing 12 provides for differences or irregularities in patient anatomy and can enhance the study through precise head positioning.

We claim:

1. A head holder apparatus for a magnetic resonance imaging/spectroscopy unit comprising:
    a helmet adapted to be worn on the head of a user, said helmet having a front facial opening, a rear portion and a pair of side portions, the rear portion and side portions being integral with each other;
    a flexible head band; first means for shiftably connecting the band to the rear portion of the helmet;
    second means for shiftably connecting the head band to the side portions of the helmet;
    third means for adjustably mounting the band on the head of the user; and
    fourth means coupled with the band for adjustably positioning the band in an operative location with reference to the facial opening of the helmet.

2. An apparatus as set forth in claim 1, wherein the band has a pair of opposed ends, said third means adjustably coupling the ends of the band together to form a head-receiving loop, said third being movable to adjust the length of the head-receiving loop.

3. An apparatus as set forth in claim 1, wherein the band has an inner peripheral surface, and including a plurality of cushions on the inner surface of the band for engaging the head of the user.

4. Apparatus for positioning the head of the a user in a fixed position relative to an MR imaging/spectroscopy system comprising:
    a flexible head band adapted to be worn around the head of the user, said band having a pair of ends which are separable from each other;
    means adjustably coupling the ends of the band together; and
    head gear including a helmet having a front facial opening and adapted to be worn on the head of the user and a ball joint structure coupled with the band for adjustably positioning the band in an operative position with reference to the head of the user.

5. An apparatus as set forth in claim 4, wherein said band has a rear part and the helmet has a rear portion, said head gear includes a stabilizing bar coupling the rear part of the band to the rear portion of the helmet.

6. An apparatus as set forth in claim 5, further comprising a fastener, said stabilizing bar having a vertical slot for receiving the fastener for adjustable attachment of said head band.

7. An apparatus as set forth in claim 4, wherein the means for coupling the ends of the band together include a worm gear.

8. An apparatus as set forth in claim 4, further comprising a plurality of cushions on the inner surface of the band adapted for engaging the outer surface of the head of the user.

9. An apparatus as set forth in claim 4, wherein said helmet is a rigid member which includes said facial opening and a rear portion, and means on the rear portion of the helmet for securing the head band to the helmet.

10. An apparatus as set forth in claim 4, said ball joint structure being on each side, respectively, of the helmet for adjustably shifting the head band relative to the helmet.

11. An apparatus as set forth in claim 4, wherein said head gear includes a stabilizer bar having a central slot therein, and a fastener carried by the stabilizer bar and extending through the slot for adjustably mounting the head band in a fixed position relative to the helmet.

12. A head holder apparatus for a magnetic resonance imaging/spectroscopy unit comprising:
    a helmet adapted to be worn on the head of a user, said helmet having a front facial opening, a rear portion and a pair of side portions, the rear portion and side portions being integral with each other;
    a flexible head band;
    first means for shiftably connecting the band to the rear portion of the helmet;
    second means for shiftably connecting the head band to the side portions of the helmet;
    third means for adjustably mounting the band on the head of the user; and
    fourth means coupled with the band for adjustably positioning the band in an operative location with reference to the facial opening of the helmet, said first means including a stabilizing bar adjustably secured to the rear portion.

13. A head holder apparatus for a magnetic resonance imaging/spectroscopy unit comprising:
    a helmet adapted to be worn on the head of a user, said helmet having a front facial opening, a rear portion and a pair of side portions, the rear portion and side portions being integral with each other;
    a flexible head band;
    first means for shiftably connecting the band to the rear portion of the helmet;
    second means for shiftably connecting the head band to the side portions of the helmet;
    third means for adjustably mounting the band on the head of the user; and
    fourth means coupled with the band for adjustably positioning the band in an operative location with reference to the facial opening of the helmet, said first means including an upright bar having a vertical slot therein, and further comprising a fastener for insertion in said slot for adjustable attachment of the bar to said helmet in a position relative to the head band.

14. A head holder apparatus for a magnetic resonance imaging/spectroscopy unit comprising:
    a helmet adapted to be worn on the head of a user said helmet having a front facial opening, a rear portion and a pair of side portions, the rear portion and side portions being integral with each other;
    a flexible head band;
    first means for shiftably connecting the band to the rear portion of the helmet;
    second means for shiftably connecting the head band to the side portions of the helmet;
    third means for adjustably mounting the band on the head of the user;
    fourth means coupled with the band for adjustably positioning the band in an operative location with reference to the facial opening of the helmet; and
    means on the helmet for securing the helmet to said imaging/spectroscopy unit.

15. A head holder apparatus for a magnetic resonance imaging/spectroscopy unit comprising:
    a helmet adapted to be worn on the head of a user, said helmet having a front facial opening, a rear portion and a pair of side portions, the rear portion and side portions being integral with each other;
    a flexible head band;
    first means for shiftably connecting the band to the rear portion of the helmet;
    second means for shiftably connecting the head band to the side portions of the helmet;
    third means for adjustably mounting the band on the head of the user; and
    fourth means coupled with the band for adjustably positioning the band in an operative location with reference to the facial opening of the helmet, said second means including a universal joint.

16. A head holder apparatus for a magnetic resonance imaging/spectroscopy unit comprising:
    a helmet adapted to be worn on the head of a user, said helmet having a front facial opening, a rear portion and a pair of side portions, the rear portion and side portions being integral with each other;
    a flexible head band;
    first means for shiftably connecting the band to the rear portion of the helmet;
    second means for shiftably connecting the head band to the side portions of the helmet;
    third means for adjustably mounting the band on the head of the user; and
    fourth means coupled with the band for adjustably positioning the band in an operative location with reference to the facial opening of the helmet, the second means including a ball joint for each side portion respectively, of the helmet.

17. An apparatus as set forth in claim 16, wherein said first means includes a stabilizer bar having a central slot therein, and a fastener carried by the helmet and extending through the slot for adjustably mounting the bar, and thereby the helmet in a fixed position relative to the band.

* * * * *

UNITED STATES PATENT AND TRADEMARK OFFICE
CERTIFICATE OF CORRECTION

PATENT NO. : 5,388,580
DATED : February 14, 1995
INVENTOR(S) : James V. Sullivan, Joseph A. Frank and Ronald W. Seldon It is certified that error appears in the above-indentified patent and that said Letters Patent is hereby corrected as shown below:

Col. 2, line 19, before "devices", erase ".".

Col. 4, line 36 (Claim 1, line 7), "first means for shiftably connect-" should be moved one line down as it is a separate element of the claim.

Col. 4, line 48 (Claim 2, line 4), after "third", insert --means--..

Signed and Sealed this

Twenty-sixth Day of December, 1995

Attest:

BRUCE LEHMAN

*Attesting Officer*  *Commissioner of Patents and Trademarks*